United States Patent [19]

Anderson

[11] 3,973,017

[45] Aug. 3, 1976

[54] IMIDAZOTHIAZINES, DERIVATIVES AND ANALOGUES THEREOF

[75] Inventor: Paul S. Anderson, Lansdale, Pa.

[73] Assignee: Merck & Co., Inc., Rahway, N.J.

[22] Filed: July 7, 1975

[21] Appl. No.: 593,412

[52] U.S. Cl.............................. 424/246; 424/248; 424/250; 260/247.5 EP; 260/268 BC
[51] Int. Cl.²................. C07D 279/16; A61K 31/54
[58] Field of Search............... 260/243 R, 247.5 EP, 260/268 BC; 424/246, 248, 250

[56] References Cited
UNITED STATES PATENTS 3,835,144   9/1974   Denzel et al................. 260/268 BC Primary Examiner—John M. Ford
Attorney, Agent, or Firm—Harry E. Westlake, Jr.; James A. Arno; William H. Nicholson

[57] ABSTRACT

Disclosed are 2,3,5,6-tetrahydro-8H-imidazo-[2,1-c][1,4]thiazines, analogues and derivatives thereof which are effective in inhibiting indoleamine-N-methyl transferase and thus useful in the treatment of mental aberrations, such as schizophrenia. Also disclosed are processes for the preparation of such imidazothiazines; pharmaceutical compositions comprising such compounds; and methods of treatment comprising administering such compounds and compositions.

7 Claims, No Drawings

IMIDAZOTHIAZINES, DERIVATIVES AND ANALOGUES THEREOF

BACKGROUND OF THE INVENTION

This invention relates to certain imidazothiazines and to certain analogues and derivatives thereof which by virtue of their ability to inhibit indoleamine-N-methyl transferase are useful in the treatment of certain mental aberrations in man, such as schizophrenia. Such compounds will collectively hereinafter, for convenience, be referred to as "bicyclic amidines" because of the common structural unit which relates the compounds of the present invention. This invention also relates to processes for the preparation of such bicyclic amidines; to pharmaceutical compositions comprising such bicyclic amidines; and to methods of treatment comprising administering such compounds and compositions when indicated for the treatment of mental aberrations such as schizophrenia. The bicyclic amidines of the present invention may be depicted by the following generic structure (I):

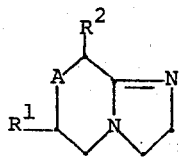

wherein:
A is S, O, or NR (R is selected from the group consisting of hydrogen, lower alkyl, or lower alkoxycarbonyl);
and $R^1$ and $R^2$ are independently selected from the group consisting of hydrogen, halogen such as chloro, lower alkyl, or lower alkoxycarbonyl.

N,N-dimethylindoleamines are generally psychotomimetic agents and some of these (e.g., dimethylserotonin and dimethyltryptamine) are reported to be produced in excessive amounts by individuals with certain mental aberrations, most commonly classified as schizophrenic. Indoleamino-N-methyl transferase catalyzes the methylation steps in the biosynthesis of these compounds. Accordingly, inhibitors of this enzyme are of therapeutic value in management of the body chemistry of patients having mental aberrations such as schizophrenia and thus are useful in alleviating some of the symptons of the disease. Thus it is an object of the present invention to provide the above-described bicyclic amidines and their pharmaceutically acceptable N-acid addition salts; to provide processes for the preparation of such compounds; pharmaceutical compositions comprising such compounds; and to provide methods of treatment comprising administering such compounds and compositions, when indicated for the treatment/management of mental aberrations such as schizophrenia.

DETAILED DESCRIPTION OF THE INVENTION

The preferred bicyclic amidines of the present invention are structurally depicted below:

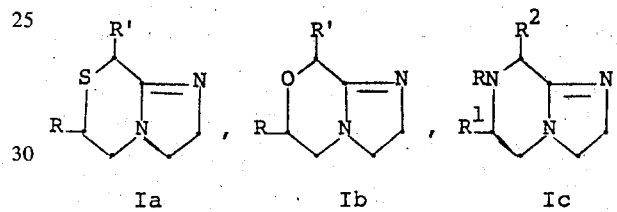

Ia          Ib          Ic wherein $R^1$ and $R^2$ are independently selected from the group consisting of hydrogen, chloro, lower alkyl having from 1 to about 6 carbon atoms, or lower alkoxycarbonyl having from 2 to about 7 carbon atoms; and R is selected from the group consisting of hydrogen, lower alkyl having from 1 to about 6 carbon atoms, or lower alkoxycarbonyl having from 2 to about 7 carbon atoms.

In general, the compounds of the present invention are prepared according to the following scheme:

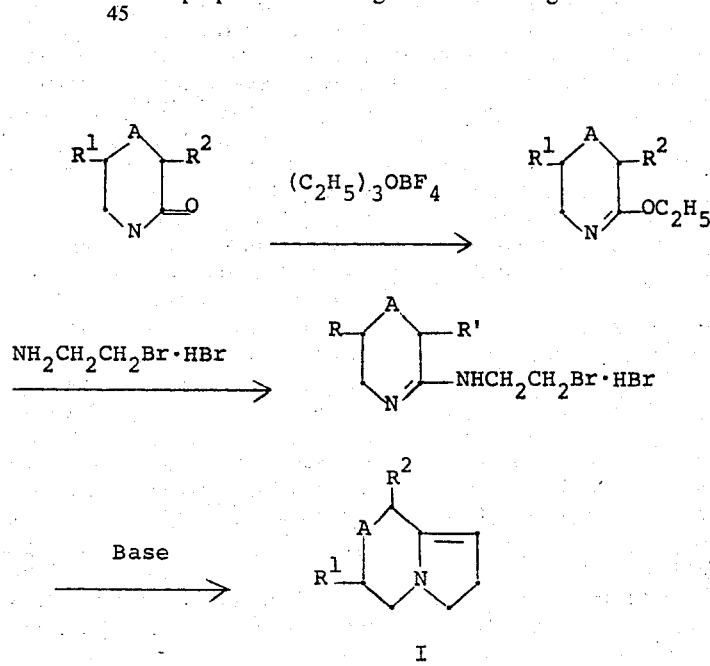

I

In words, relative to the above diagram, an appropriately substituted lactam is treated with an alkylating agent such as trialkyloxonium fluoroborate (e.g., trimethyl-, triethyl- or the like) in a solvent such as methylenechloride, chloroform and the like at 0° to about 25°C. for from 1 to about 6 hours. The resulting lactam ether is then reacted with a 2-haloethylamine hydrohalide such as 2-bromo-ethylamine hydrobromide in a solvent such as methanol, ethanol, DMF or the like at 25° to 75°C. for from 1 to 5 hours. The resulting amidine is then cyclized to the final product I by treatment with a strong base such as an alkali metal alkoxide, for example: sodium methoxide, sodium ethoxide, or hydrous oxide such as sodium hydroxide or the like in a solvent such as methanol, ethanol, DMF or the like.

Also contemplated within the scope of the present invention are pharmaceutically acceptable N-acid addition salts of the bycyclic amidines of the present invention represented by structural formula I. Such pharmaceutically acceptable forms, prepared by conventional means, include: the hydrochloride, hydrobromide, sulfate, phosphate, citrate, tartrate, succinate and the like. These pharmaceutically acceptable salts of I are generally equivalent in potency to the free amino form of I taking into consideration the stoichiometric quantities employed.

In the method of treatment and pharmaceutical composition aspects of the present invention, the daily dose can be from about 0.005 mg./kg. to about 300 mg./kg. per day and preferably from 0.05 mg./kg. to 100 mg./kg. per day, bearing in mind, of course, that in selecting the appropriate dosage in any specific case, consideration must be given to the individual's weight, general health, metabolism, age and other factors which influence response to the drug.

Another embodiment of this invention is the provision of pharmaceutical compositions in dosage unit form which comprise from about 1 mg. to 500 mg. of a compound of the above formula.

The pharmaceutical compositions may be in a form suitable for oral use, for example, as tablets, solutions, aqueous or oily suspension, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate or sodium phosphate; granulating and disintegrating agents, for example maize starch and alginic acid; binding agents, for example starch, gelatin or acacia, and lubricating agents, for example magnesium stearate, stearic acid or talc. The tablets may be uncoated or they may be coated by known techniques to delay disintegration and adsorption in the gastro-intestinal tract and thereby provide a sustained action over a longer period.

Formulations for oral use may also be presented as hard gelatin capsules wherein the active ingredient is mixed with an inert solid diluent, for example calcium carbonate, calcium phosphate or dalin, or as soft gelatin capsules wherein the active ingredient is dissolved or mixed with an oil or aqueous medium, for example arachis oil, liquid paraffin, olive oil or water by itself.

Aqueous suspensions or solutions containing the active compound in admixture with excipients are suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxy-cetanol, or condensation products of ethylene oxide with partial esters derived from fatty acids and a hexitol, for example polyoxyethylene sorbitol mon-oleate, or condensation products of ethylene oxide with partial esters derived from fatty acids and hexitol anhydrides, for example polyoxyethylene sorbitan mono-oleate. The aqueous suspensions may also contain one or more preservatives, for example ethyl or n-propyl, p-hydroxy benzoate, one or more coloring agents, one or more flavoring agents and one or more sweetening agents, such as sucrose, saccharin, or sodium or calcium cyclamate.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid parafin or mixtures of these. Suitable emulsifying agents may be naturally-occurring gums, for example gum acacia or gum tragacanth, naturally-occurring phosphatides, for example soya bean lecithin, and esters of partial esters derived from fatty acids and hexitol anhydrides, for example sorbitan mon-oleate, and condensation products of the said partial esters with ethylene oxide, for example polyoxyethylene sorbitan mon-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous solution or suspension. This aqueous medium may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol.

The pharmaceutical compositions may be tableted or otherwise formulated so that for every 100 parts by weight of the composition there are present between 5 and 95 parts by weight of the active ingredient. The dosage unit form will generally contain between about 0.05 mg. and about 500 mg. of the active ingredient of the formulae stated above.

From the foregoing formulation discussion it is apparent that the compositions of this invention can be administered orally or parenterally. The term parenteral as used herein includes subcutaneous injection, intravenous, intramuscular, or intrasternal injection or infusion techniques. In addition, the compounds can be given rectally as suppositories or topically with peneetrants.

The following examples further illustrate but do not limit the product, process, compositional or method of treatment aspects of the present invention.

EXAMPLE 1

Preparation of 2,3,5,6-tetrahydro-8H-imidazo[2,1-c][1,4]-thiazine

A solution of 23.4 g. (0.20 moles) of 3-thiomorpholinone in 150 ml. dry $CH_2Cl_2$ is added dropwise with stirring to a solution of 44 grams of triethyloxonium fluoroborate in 100 ml. of $CH_2Cl_2$ maintained at 0°–5°C. Stirring is continued for six hours as temperature is allowed to come to 25°C; $K_2CO_3$ (46 g.) is added and the methylene chloride solution is decanted and the residue of $K_2CO_3$ is washed with $CH_2Cl_2$. The combined organic solutions are dried over anhydrous $K_2CO_3$, filtered and solvent evaporated. Distillation of the concentrate gives 17.9 g. of the lactam ether. The lactam ether is added to a solution of 24.6 grams (0.12 moles) of 2-bromo-ethylamine hydrobromide in 150 ml. absolute ethanol and the resulting solution heated on a steam bath for two hours. The solvent is evaporated and the residue washed with ether. The resulting crystalline material is washed with acetone and air dried under suction. The crude crystalline product (28.5 g.) is dissolved in 200 ml. ethanol and sodium methoxide (.07 mole in 50 ml. methanol is added; the resulting solution is heated under reflux with stirring for two hours prior to evaporation of the solvent under reduced pressure. To the residue is added 75 ml. water and the solution made basic with potassium carbonate; the basic solution is extracted with chloroform (3 × 100 ml.). The combined extracts are dried over anhydrous $Na_2SO_4$, filtered and the solvent evaporated. Distillation of the concentrate gives 2,3,5,6-tetrahydro-8H-imidazo[2,1-c][1,4]thiazine (11.3 g.). The hydrochloride and oxalate salts are prepared, respectively, by dissolving 1 g. of the product in the minimum volume of absolute ethanol at 45°C. and adding dropwise an aqueous 1 molar solution of the respective acid; the resulting salts are collected by filtration, washed with ethanol and dried.

EXAMPLE 2

Preparation of 2,3,5,6-tetrahydro-8H-imidazo[2,1-c][1,4]-oxazine hydrogen fumarate A solution of 3-morpholinone (10.5 g.) in methylenechloride (100 ml.) is added dropwise with stirring at 0°C. to a solution of triethyloxonium fluoroborate (24 g.) in methylene chloride (200 ml.). The solution is stirred for 6 hours and then treated with 26 g. of 50% aqueous potassium carbonate solution. The organic solution is separated, dried over $K_2SO_3$, filtered and the filtrate concentrated under reduced pressure. Distillation of the residue gives the lactam ether, b.p. 68°/20 mm., 8.1 g. A solution of lactam ether and 2-bromoethylamine hydrobromide (12.7 g.) in ethanol (100 ml.) is heated under reflux for one hours, treated with sodium methoxide (3.2 g.) and heated under reflux for one additional hour. The solvent is evaporated, the residue treated with aqueous sodium hydroxide solution and them extracted with chloroform. The chloroform extract is dried over $Na_2SO_4$, filtered and the filtrate concentrated under reduced pressure. The concentrate on distillation yields 5.2 g. of product, b.p. 107°–9°C. 18 mm. which is added to fumaric acid in hot isopropanol to yield on cooling the hydrogen fumarate, m.p. 179°–182°C.

Analysis Calc. for: $C_{10}H_{14}N_2O_5$:
Calc.: C, 49.58; H, 5.83; N, 11.57.
Found: C, 49.10; H, 6.04; N, 11.40.

EXAMPLE 3

Preparation of ethyl 2,3,5,6,7,8-hexahydroimidazao[1,2-a]-pyrazine-7-carboxylate

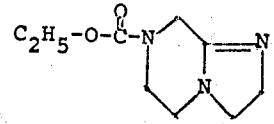

A solution of ethyl 3-ketopiperazin-1-yl carbamate (25 g., .15 moles) in 100 ml. of methylene chloride is added dropwise with stirring at 0°C. to a solution of triethyloxonium fluoroborate (32 g.) in 200 ml. of methylenechloride. After six hours of stirring, the solution is treated with 36 g. of 50% aqueous potassium carbonate solution. The organic solution is separated, dried over anhydrous $K_2CO_3$, filtered and the filtrate concentrated under reduced pressure. The concentrate is distilled to yield 6 g. of lactam ether b.p. 80°–85°/0.2 mm. A solution of the lactam ether and 2-bromoethylamine hydrobromide (6.1 g.) in ethanol (150 ml.) is allowed to stand for 2 days. This solution is heated under reflux for one hour after adding 1.8 g. of sodium methoxide. The solvent is evaporated, the residue treated with aqueous sodium hydroxide solution and then extracted with chloroform. The chloroform solution is dried over $Na_2SO_4$, filtered and the filtrate contrated under reduced pressure. Distillation of the concentrate gives the product, b.p. 166°–168°/4 mm.

Analysis Calc. for: $C_9H_{15}N_3O_2$:
Calc.: C, 54.81; H, 7.66; N, 21.29.
Found: C, 54,40; H, 7.75; N, 21,51.

EXAMPLE 4

Following the procedure of Example 1, the following compounds of the present invention, given in the table below, are prepared when the appropriate substitution (in equivalent amount) for the 3-thiomorpholinone of Example 1 is made:

TABLE I

| COMPOUND | A | R¹ | R² | REAGENT, USED IN PLACE OF LACTAM OF EXAMPLE 1 |
|---|---|---|---|---|
| 1.) | S | CH₃ | H | |
| 2.) | S | H | CH₃ | |
| 3.) | O | CH₃ | H | |
| 4.) | O | H | CH₃ | |
| 5.) | S | C₆H₅ | H | |

EXAMPLE 5

Pharmaceutical compositions

A typical tablet containing 5 mg. of 2,3,5,6-tetrahydro-8H-imidazo[2,1-c][1,4]-thiazine per tablet is prepared by mixing together with the active ingredient calcium phosphate, lactose and starch in the amounts shown in the tables below. After these ingredients are thoroughly mixed, the dry mixture blended for an additional three minutes. This mixture is then compressed into tablets weighing approximately 129 mg. each. Similarly prepared are tablets containing 2,3,5,6-tetrahydro-8H-imidazo[2,1-c][1,4]-oxazine and ethyl 2,3,5,6,7,8-hexahydroimidazo[1,2-a]-pyrazine-7-carboxylate.

| TABLET FORMULA | |
|---|---|
| INGREDIENT | MG. PER TABLET |
| 2,3,5,6-Tetrahydro-8H-imidazo-[2,1-c][1,4]-thiazine | 5 mg. |
| Calcium phosphate | 52 mg. |
| Lactose | 60 mg. |
| Starch | 10 mg. |
| Magnesium stearate | 1 mg. |

| TABLET FORMULA | |
|---|---|
| INGREDIENT | MG. PER TABLET |
| 2,3,5,6-Tetrahydro-8H-imidazo-[2,1-c][1,4]-oxazine | 5 mg. |
| Calcium phosphate | 52 mg. |
| Lactose | 60 mg. |
| Starch | 10 mg. |
| Magnesium stearate | 1 mg. |

| TABLET FORMULA | |
|---|---|
| INGREDIENT | MG. PER TABLET |
| Ethyl 2,3,5,6,7,8-hexahydroimidazo-[1,2-a]-pyrazine-7-carboxylate | 5 mg. |
| Calcium phosphate | 52 mg. |
| Lactose | 60 mg. |
| Starch | 10 mg. |
| Magnesium stearate | 1 mg. |

What is claimed is:

1. A compound having the structure:

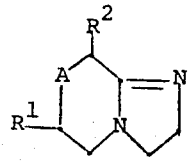

wherein A is selected from the group consisting of S, O, and NR; and wherein R is selected from the group consisting of hydrogen, lower alkyl, or lower alkoxycarbonyl; and R¹ and R² are independently selected from the group consisting of hydrogen, halogen, lower alkyl, and lower alkoxy carbonyl; and the pharmaceutically acceptable N-acid addition salts thereof.

2. A compound according to claim 1 which is 2,3,5,6-tetrahydro-8H-imidazo[2,1-c][1,4]-thiazine.

3. A compound according to claim 1 which is 2,3,5,6-tetrahydro-8H-imidazo[2,1-c][1,4]-oxazine.

4. A compound according to claim 1 which is ethyl 2,3,5,6,7,8-hexahydroimidazo[1,2-a]-pyrazine-7-carboxylate.

5. A process for preparing a compound having the structure:

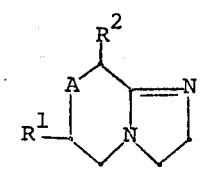

thereof which comprises cyclizing in the presence of base a compound having the structure:

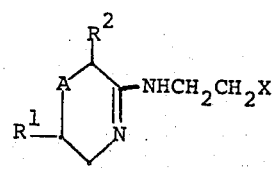

wherein X is halogen;
A is selected from the group consisting of S, O, NR;
$R^1$ and $R^2$ are independently selected from the group consisting of hydrogen, halogen, lower alkyl, or lower alkoxy carbonyl; and R is selected from the group consisting of hydrogen, lower alkyl, and lower alkoxycarbonyl.

6. A pharmaceutical composition comprising a therapeutically effective amount in unitary dosage form of a compound having the structure:

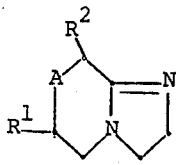

wherein A is selected from the group consisting of S, O, and NR; and wherein R is selected from the group consisting of hydrogen, lower alkyl, or lower alkoxy carbonyl; and $R^1$ and $R^2$ are independently selected from the group consisting of hydrogen, halogen, lower alkyl, and lower alkoxycarbonyl; and the pharmaceutically acceptable N-acid addition salts thereof; and a pharmaceutical carrier therefor.

7. A method of treatment comprising administering a therapeutically effective amount in unitary dosage form of a compound having the structure:

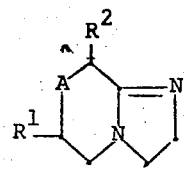

wherein A is selected from the group consisting of S, O, and NR; and wherein R is selected from the group consisting of hydrogen, lower alkyl, or lower alkoxy carbonyl; and $R^1$ and $R^2$ are independently selected from the group consisting of hydrogen, halogen, lower alkyl, and lower alkoxycarbonyl; and the pharmaceutically acceptable N-acid addition salts thereof.

\* \* \* \* \*